US008334268B2

(12) United States Patent
Andersch et al.

(10) Patent No.: US 8,334,268 B2
(45) Date of Patent: Dec. 18, 2012

(54) INSECTICIDAL ACTIVE INGREDIENT COMBINATIONS (FORMONONETINS + INSECTICIDES)

(75) Inventors: Wolfram Andersch, Gladbach (DE); Heike Hungenberg, Langenfeld (DE); Darren Mansfield, Kürten (DE)

(73) Assignee: Plant Health Care, Inc., Pittsburgh, PA (US)

( * ) Notice: Subject to any disclaimer, the term of this patent is extended or adjusted under 35 U.S.C. 154(b) by 127 days.

(21) Appl. No.: 12/515,954

(22) PCT Filed: Nov. 16, 2007

(86) PCT No.: PCT/EP2007/009898
§ 371 (c)(1),
(2), (4) Date: May 29, 2009

(87) PCT Pub. No.: WO2008/064778
PCT Pub. Date: Jun. 5, 2008

(65) Prior Publication Data
US 2010/0048497 A1   Feb. 25, 2010

(30) Foreign Application Priority Data
Nov. 29, 2006 (DE) .......... 10 2006 056 544

(51) Int. Cl.
*A61K 31/70* (2006.01)
*A61K 31/535* (2006.01)
*A61K 31/44* (2006.01)
*A61K 31/425* (2006.01)
*A61K 31/415* (2006.01)
*A61K 31/35* (2006.01)

(52) U.S. Cl. ....... 514/28; 514/229.2; 514/341; 514/365; 514/407; 514/456

(58) Field of Classification Search .......... None
See application file for complete search history.

(56) References Cited

U.S. PATENT DOCUMENTS

| | | | |
|---|---|---|---|
| 2,758,115 A | 8/1956 | Lorenz | |
| 3,264,177 A | 8/1966 | Kenaga | |
| 3,309,266 A | 3/1967 | Magee | |
| 3,577,543 A | 5/1971 | Baranyovits et al. | |
| 4,053,634 A | 10/1977 | Bellina et al. | |
| 4,742,060 A | 5/1988 | Shiokawa et al. | |
| 4,962,126 A | 10/1990 | Drabek | |
| 5,002,603 A * | 3/1991 | Safir et al. .......... | 504/100 |
| 5,478,855 A | 12/1995 | Suzuki et al. | |
| 2008/0139388 A1 | 6/2008 | Krohn et al. | |

FOREIGN PATENT DOCUMENTS

| | | |
|---|---|---|
| EP | 0210487 | 2/1987 |
| EP | 0234045 | 9/1987 |
| EP | 0347488 | 12/1989 |
| WO | 93/10083 | 5/1993 |
| WO | 9637494 | 11/1996 |
| WO | 9728150 | 8/1997 |
| WO | 9825923 | 6/1998 |
| WO | 0054568 | 9/2000 |
| WO | 2008086948 | 7/2008 |
| WO | 2008092580 | 8/2008 |
| WO | 2008103422 | 8/2008 |

OTHER PUBLICATIONS

Park et al (Immunology 116:711-81, 2005).*
Solntsev et al (Izvestiya Akademii Nauk SSSR, Seriya Biologicheskaya 6:862-870, 1990—Abstract only).*
Buffin (Pesticide News 62:22-23, 2003).*
Yue et al (J Econ Entomol 96:503-509, 2003).*
York et al (Weed Science 41:269-280, 1993—p. 269 only).*
PCT/EP2007/009898 Written Opinion of the International Searching Authority and English Translation, dated May 29, 2009 (13 pages).
International Search Report (ISR) for PCT/EP2007/009898, dated Nov. 28, 2008 (6 pages).

* cited by examiner

*Primary Examiner* — Craig Ricci
(74) *Attorney, Agent, or Firm* — Buchanan Ingersoll & Rooney PC

(57) ABSTRACT

The present invention relates to novel active compound combinations consisting, firstly, of formononetin and, secondly, of known insecticidally active compounds, which active compound combinations are highly suitable for controlling unwanted animal pests, such as insects or acarids, or nematodes.

7 Claims, No Drawings

INSECTICIDAL ACTIVE INGREDIENT COMBINATIONS (FORMONONETINS + INSECTICIDES)

CROSS REFERENCE TO RELATED APPLICATIONS

This application is a 371 National Stage Application of PCT/EP2007/009898 filed Nov. 16, 2007 which claims priority to German Application 10 2006 056 544.4 filed Nov. 29, 2006.

BACKGROUND OF THE INVENTION

1. Field of the Invention

The present invention relates to novel active compound combinations consisting, firstly, of formononetin and, secondly, of known insecticidally active compounds. These active compound combinations are highly suitable for controlling unwanted animal pests, such as insects or acarids, and also phytoparasitic nematodes.

2. Description of Related Art

It is already known that formononetin of the formula (I),

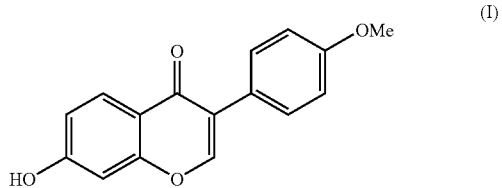

an isoflavone produced by red clover (*Trifolium pratens*), enhances the growth of the roots of useful plants (U.S. Pat. No. 5,002,603).

Furthermore, it is known that numerous chloronicotinyls, phosphoric esters, carbamates, heterocycles, organotin compounds, benzoylureas and pyrethroids have insecticidal, acaricidal and nematicidal properties (cf., for example, EP 0 192 060, U.S. Pat. No. 2,758,115, U.S. Pat. No. 3,309,266, GB 1,181,657, WO 93/22297 A1, WO 93/10083 A1, DE 26 41 343 A1, EP 347 488 A1, EP 210 487 A1, U.S. Pat. No. 3,264,177 and EP 234 045 A2). However, the activity of these compounds is not in all respects satisfactory.

SUMMARY OF THE INVENTION

Surprisingly, it has now been found that formononetin increases the activity of insecticidally, acaricidally or nematicidally active compounds.

Furthermore, surprisingly, it has been found that insecticidally, acaricidally or nematicidally active compounds increase the yield or the growth of crop plants treated with formononetin, exceeding the effect of a treatment with formononetin alone or a treatment with the insecticidally, acaricidally or nematicidally active compounds alone or exceeding the sum of both individual activities.

This invention now provides novel active compound combinations having very good properties for controlling insects, arachnids or phytoparasitic nematodes, which combinations, in addition to formononetin, comprise at least one active compound selected from groups (2) to (24) below.
group (2) acetylcholine receptor agonists/antagonists (such as, for example, chloronicotinyls/neonicotinoids);
group (3) acetylcholinesterase (ACHE) inhibitors (such as, for example, carbamates and organophosphates);
group (4) sodium channel modulators/blockers of voltage-gated sodium channels (such as, for example, pyrethroids and oxadiazines);
group (5) acetylcholine receptor modulators (such as, for example, spinosyns);
group (6) antagonists of GABA-gated chloride channels (such as, for example, cyclodiene organochlorines and fiproles);
group (7) chloride channel activators (such as, for example, mectins);
group (8) juvenile hormone mimetics;
group (9) ecdyson agonists/disruptors (such as, for example, diacylhydrazines);
group (10) inhibitors of chitin biosynthesis (such as, for example, benzoylureas);
group (11) inhibitors of oxidative phosphorylation, ATP disruptors (such as, for example, organotins);
group (12) uncouplers of oxidative phosphorylation acting by interrupting the H-proton gradient (such as, for example, pyrroles and dinitrophenols);
group (13) side-I electron transport inhibitors (such as, for example, METIs);
group (14) side-II electron transport inhibitors;
group (15) side-III electron transport inhibitors;
group (16) microbial disruptors of the insect gut membrane;
group (17) inhibitors of fat synthesis (such as, for example, tetronic acids and tetramic acids);
group (18) carboxamides;
group (19) octopaminergic agonists;
group (20) inhibitors of magnesium-stimulated ATPase;
group (21) phthalamides;
group (22) nereistoxin analogues;
group (23) biologicals, hormones or pheromones;
group (24) active compounds with unknown or unspecific mechanisms of action (such as, for example, fumigants, selective antifeedants and mite growth inhibitors).

Surprisingly, the insecticidal or acaricidal activity of the active compound combination according to the invention is considerably higher than the sum of the activities of the individual active compounds. Accordingly, an unforeseeable synergistic effect is present, and not just an addition of activities.

In addition to at least one isopentylcarboxanilide of the general formula (I), the active compound combinations according to the invention comprise at least one active compound selected from groups (2) to (24).

The active compounds of groups (2) to (24) comprise a large number of possible mixing partners listed below. Most of these active compounds are commercially available and/or listed in the Pesticide Manual (The Pesticide Manual, 13th edition, Editor: CDS Tomlin, British Crop Protection Council, ISBN 1 901396 13 4). Active compounds not currently available or not listed in the Pesticide Manual are identified unambiguously by their IUPAC name.

DETAILED DESCRIPTION OF A PREFERRED EMBODIMENT

Group (2) of the acetylcholine receptor agonists/antagonists specifically includes the following active compounds: (2.1) chloronicotinyls/neonicotinoids (for example acetamiprid, clothianidin, dinotefuran, imidacloprid, nitenpyram, nithiazine, thiacloprid, thiamethoxam, imidaclotiz ((2E)-1-[(2-chloro-1,3-thiazol-5-yl)methyl]-N-nitroimidazolidin-2- imine), AKD 1022 ((2E)-1-[(2-chloro-1,3-thiazol-5-yl)methyl]-3,5-dimethyl-N-nitro-1,3,5-triazinan-2-imine));
(2.2) nicotines, bensultap, cartap.

The active compound combinations according to the invention preferably comprise the following acetylcholine receptor agonists/antagonists of group (2):
(2.1.1) clothianidin
(2.1.2) imidacloprid
(2.1.3) thiacloprid
(2.1.4) thiamethoxam
(2.1.5) acetamiprid
(2.1.6) dinotefuran
(2.1.7) nitenpyram
(2.1.8.) imidaclotiz The active compound combinations according to the invention particularly preferably comprise the following acetylcholine receptor agonists/antagonists of group (2):
(2.1.1) clothianidin
(2.1.2) imidacloprid
(2.1.3) thiacloprid
(2.1.4) thiamethoxam
(2.1.5) acetamiprid Group (3) of the acetylcholinesterase (AChE) inhibitors specifically includes the following active compounds:
(3.1) carbamates (for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, chloethocarb, dimetilan, ethiofencarb, fenobucarb, fenothiocarb, formetanate, furathiocarb, isoprocarb, metam-sodium, methiocarb, methomyl, metolcarb, oxamyl, phosphocarb, pirimicarb, promecarb, propoxur, thiodicarb, thiofanox, triazamate, trimethacarb, XMC, xylylcarb);
(3.2) organophosphates (for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl-ethyl), coumaphos, cyanofenphos, cyanophos, chlorfenvinphos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemetonmethyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion).

The active compound combinations according to the invention preferably comprise the following acetylcholinesterase (AChE) inhibitors of group (3):
(3.1.1) methiocarb
(3.1.2) thiodicarb
(3.1.3) ethoprophos
(3.1.4) aldicarb
(3.1.5) fenamiphos
(3.2.1) tebupirimphos
(3.2.2) cadusaphos
(3.2.3) oxamyl
(3.2.4) fosthiazate
chlorpyriphos-(methyl-/ethyl)

The active compound combinations according to the invention particularly preferably comprise the following acetylcholinesterase (ACHE) inhibitors of group (3):
(3.1.1) methiocarb
(3.1.2) thiodicarb
(3.1.3) aldicarb
(3.2.1) ethoprophos
(3.2.2) fenamiphos Group (4) of the sodium channel modulators/blockers of voltage-gated sodium channels specifically includes the following active compounds:
(4.1) pyrethroids [for example acrinathrin, allethrin (d-cis-trans, d-trans), beta-cyfluthrin, bifenthrin, bioallethrin, bioallethrin-S-cyclopentyl-isomer, bioethanomethrin, biopermethrin, bioresmethrin, chlovaporthrin, cis-cypermethrin, cis-resmethrin, cis-pennethrin, clocythrin, cycloprothrin, cyfluthrin, cyhalothrin, cypermethrin (alpha-, beta-, theta-, zeta-), cyphenothrin, DDT, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, pennethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R-isomer), tralocythrin, tralomethrin, transfluthrin, ZXI 8901, pyrethrins (pyrethrum)];
(4.2) oxadiazines (for example indoxacarb).

The active compound combinations according to the invention preferably comprise the following sodium channel modulators/blockers of voltage-gated sodium channels of group (4):
(4.1.1) beta-cyfluthrin
(4.1.2) cyfluthrin
(4.1.3) deltamethrin
(4.1.4) tefluthrin
(4.1.5) bifenthrin
(4.2.1) indoxacarb The active compound combinations according to the invention particularly preferably comprise the following sodium channel modulators/blockers of voltage-gated sodium channels of group (4):
(4.1.1) beta-cyfluthrin
(4.1.2) cyfluthrin
(4.1.3) deltamethrin
(4.1.4) tefluthrin
(4.2.1) indoxacarb Group (5) of the acetylcholine receptor modulators specifically includes the following active compounds:
(5.1) spinosyns (for example spinosad). Novel spinosyn from Dow The active compound combinations according to the invention preferably comprise the following acetylcholine receptor modulators of group (5):
(5.1.1) spinosad
(5.1.2) XDE-175, Compound of the formula (II) (known from WO 97/00265 A1, U.S. Pat. No. 6,001,981 and Pest Manag. Sci. 57, 177-185, 2001)

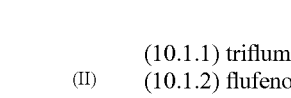

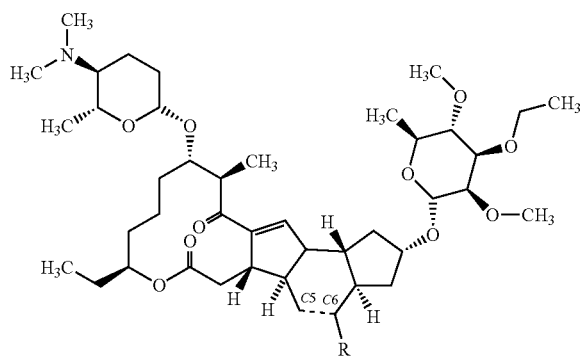

Group (6) of the antagonists of GABA-gated chloride channels specifically includes the following active compounds:
(6.1) cyclodiene organochlorines (for example camphechlor, chlordane, gamma-HCH, HCH, heptachlor, lindane, methoxychlor), except for endosulfan.
(6.2) fiproles (for example acetoprole, ethiprole, fipronil, vaniliprole).

The active compound combinations according to the invention preferably comprise the following antagonists of GABA-gated chloride channels of group (6):
(6.2.1) fipronil
(6.2.2) ethiprole Group (7) of the chloride channel activators specifically includes the following active compounds:
(7.1) mectins (for example abamectin, avermectin, emamectin, emamectin-benzoate, ivermectin, milbemectin, milbemycin)

The active compound combinations according to the invention comprise preferably the following chloride channel activators of group (7):
(7.1.1) emamectin-benzoate
(7.1.2) avermectin Group (8) of the juvenile hormone mimetics specifically includes the following active compounds: diofenolan, epofenonane, fenoxycarb, hydroprene, kinoprene, methoprene, pyriproxifen, triprene.

The active compound combinations according to the invention preferably comprise the following juvenile hormone mimetic of group (8):
(8.1.1) pyriproxifen Group (9) of the ecdyson agonists/disruptors specifically includes the following active compounds:
(9.1) diacylhydrazines (for example chromafenozide, halofenozide, methoxyfenozide, tebufenozide).

The active compound combinations according to the invention preferably comprise the following ecdyson agonist/disruptor of group (9):
(9.1.1) methoxyfenozide Group (10) of the inhibitors of chitin biosynthesis specifically includes the following active compounds:
(10.1) benzoylureas (for example bistrifluron, chlofluazuron, diflubenzuron, fluazuron, flucycloxuron, flufenoxuron, hexaflumuron, lufenuron, novaluron, noviflumuron, penfluoron, teflubenzuron, triflumuron);
(10.2) buprofezin;
(10.3) cyromazine.

The active compound combinations according to the invention preferably comprise the following inhibitors of chitin biosynthesis of group (10):
(10.1.1) triflumuron
(10.1.2) flufenoxuron Group (11) of the inhibitors of oxidative phosphorylation, ATP disruptors specifically includes the following active compounds:
(11.1) diafenthiuron;
(11.2) organotins (for example azocyclotin, cyhexatin, fenbutatin-oxide).

Group (12) of the uncouplers of oxidative phosphorylation acting by interrupting the H-proton gradient specifically includes the following active compounds:
(12.1) pyrroles (for example chlorfenapyr);
(12.2) dinitrophenols (for example binapacyrl, dinobuton, dinocap, DNOC).

Group (13) of the side-I electron transport inhibitors specifically includes the following active compounds:
(13.1) METIs (for example fenazaquin, fenpyroximate, pyrimidifen, pyridaben, tebufenpyrad, tolfenpyrad);
(13.2) hydramethylnone;
(13.3) dicofol.

The active compound combinations according to the invention preferably comprise the following side-I electron transport inhibitors of group (13):
(13.1.1) tebufenpyrad
(13.2.1) hydramethylone Group (14) of the side-II electron transport inhibitors specifically includes the following active compound:
(14.1.1) rotenone Group (15) of the side-III electron transport inhibitors specifically includes the following active compounds:
(15.1) acequinocyl, fluacrypyrim.

Group (16) of the microbial disruptors of the insect gut membrane specifically includes the following active compounds:
(16.1) *Bacillus thuringiensis* strains.

Group (17) of the inhibitors of fat synthesis specifically includes the following active compounds:
(17.1) tetronic acids (for example spirodiclofen, spiromesifen);
(17.2) tetramic acids {for example 3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester, CAS-Reg.-No.: 382608-10-8) and carbonic acid, cis-3-(2,5-dimethylphenyl)-8-methoxy-2-oxo-1-azaspiro[4.5]dec-3-en-4-yl ethyl ester (CAS-Reg.-No.: 203313-25-1)}.

The active compound combinations according to the invention preferably comprise the following inhibitors of fat synthesis of group (17):
(17.1.1) spirodiclofen
(17.1.2) spiromesifen
(17.2.1) 3-(2,5-dimethylphenyl)-8-methoxy-2-oxo-1-azaspiro[4.5]dec-3-en-4-yl ethyl carbonate Group (18) of the carboxamides specifically includes the following active compound:
(18.1.1) flonicamid Group (19) of the octopaminergic agonists specifically includes the following active compound:
(19.1.1) amitraz Group (20) of the inhibitors of magnesium-stimulated ATPase specifically includes the following active compound:
(20.1.1) propargite Group (21) of the phthalamides specifically includes the following active compounds:
(21.1.1) $N^2$-[1,1-dimethyl-2-(methylsulphonyl)ethyl]-3-iodo-$N^1$-[2-methyl-4-[1,2,2,2-tetrafluoro-1-(trifluoromethyl)ethyl]phenyl]-1,2-benzenedicarboxamide (flubendiamide, CAS-Reg.-No.: 272451-65-7)
(21.1.2) rynaxypyr of the formula (III)

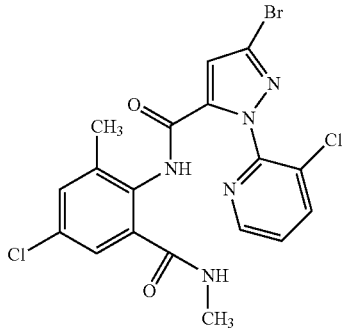

(III)

Group (22) of the nereistoxin analogues specifically includes the following active compounds:
thiocyclam hydrogen oxalate, thiosultap-sodium.

Group (23) of the biologicals, hormones or pheromones specifically includes the following active compounds: azadirachtin, *Bacillus* spec., *Beauveria* spec., codlemone, *Metarrhizium* spec., *Paecilomyces* spec., thuringiensin, *Verticillium* spec.

Group (24) of the active compounds with unknown or unspecific mechanisms of action specifically includes the following active compounds:
(24.1) fumigants (for example aluminium phosphide, methyl bromide, sulphuryl fluoride);
(24.2) selective antifeedants (for example cryolite, flonicamid, pymetrozine);
(24.3) mite growth inhibitors (for example clofentezine, etoxazole, hexythiazox);
(24.4) amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyrafluprole, pyridalyl, pyriprole, sulfluramid, tetradifon, tetrasul, triarathene, verbutin, furthermore the compound 3-methylphenyl propylcarbamate (tsumacide Z), the compound 3-(5-chloro-3-pyridinyl)-8-(2,2,2-trifluoroethyl)-8-azabicyclo[3.2.1]octane-3-carbonitrile (CAS-Reg.-Nr. 185982-80-3) and the corresponding 3-endo isomers (CAS-Reg.-Nr. 185984-60-5) (cf. WO 96/37494, WO 98/25923), and also preparations comprising insecticidally active plant extracts, nematodes, fungi or viruses.

Particularly preferred combinations according to the invention are shown in Table 1 below.

TABLE 1

| Active compound 1 | Active compound of groups (2) to (24) |
|---|---|
| formononetin | (2.1.1) clothianidin |
| formononetin | (2.1.2) imidacloprid |
| formononetin | (2.1.3) thiacloprid |
| formononetin | (2.1.4) thiamethoxam |
| formononetin | (3.1.1) methiocarb |
| formononetin | (3.1.2) thiodicarb |
| formononetin | (3.1.3) ethoprofos |

TABLE 1-continued

| Active compound 1 | Active compound of groups (2) to (24) |
|---|---|
| formononetin | (3.2.1) tebuprimophos |
| formononetin | (3.2.2) cadusaphos |
| formononetin | (3.2.3) oxamyl |
| formononetin | (4.1.1) beta-cyfluthrin |
| formononetin | (4.1.2) cyfluthrin |
| formononetin | (4.1.3) deltamethrin |
| formononetin | (4.1.4) tefluthrin |
| formononetin | (4.2.1) indoxacarb |
| formononetin | (5.1.1) spinosad |
| formononetin | (5.1.2) XDE-175 of the formula (II) |
| formononetin | (6.2.1) fipronil |
| formononetin | (6.2.2) ethiprole |
| formononetin | (7.1.1) emamectin-benzoate |
| formononetin | (8.1.1) pyriproxifen |
| formononetin | (9.1.1) methoxyfenozide |
| formononetin | (10.1.1) triflumuron |
| formononetin | (10.1.2) flufenoxuron |
| formononetin | (13.1.1) tebufenpyrad |
| formononetin | (13.2.1) hydramethylone |
| formononetin | (17.1.1) spirodiclofen |
| formononetin | (17.1.2) spiromesifen |
| formononetin | (17.2.1) 3-(2,5-dimethylphenyl)-8-methoxy-2-oxo-1-azaspiro[4.5]dec-3-en-4-yl ethyl carbonate |
| formononetin | (18.1.1) flonicamid |
| formononetin | (21.1.1) flubendiamide |
| formononetin | (21.1.2) rynaxypyr |

All active compound combinations (each row of Table 1) are independent ways of achieving the object.

According to the invention, instead of formononetin, it is also possible to use its salts, in particular its alkali metal salts.

In addition, the active compound combinations may also comprise further fungicidally, acaricidally or insecticidally active components for mixtures.

If the active compounds in the active compound combinations according to the invention are present in certain weight ratios, the synergistic effect is particularly pronounced. However, the weight ratios of the active compounds in the active compound combinations can be varied within a relatively wide range. In general, the combinations according to the invention comprise active compounds of the formula (I) and the mixing partner in the preferred mixing ratios stated in the table below, the mixing ratios being based on ratios by weight.

The ratio is to be understood as meaning formononetin:mixing partner.

TABLE 2

Mixing ratios

| Mixing partner (group) | Preferred mixing ratio | Particularly preferred mixing ratio |
|---|---|---|
| (2.1) chloronicotinyls/Neonicotinoids | 500:1 to 1:50 | 125:1 to 1:25 |
| (2.2) nicotines, bensultap, cartap | 500:1 to 1:50 | 125:1 to 1:25 |
| (3.1) carbamates | 500:1 to 1:1000 | 125:1 to 1:500 |
| (3.2) organophosphates | 500:1 to 1:50 | 125:1 to 1:25 |
| (4.1) pyrethroids | 500:1 to 1:50 | 125:1 to 1:25 |
| (4.2) oxadiazines | 500:1 to 1:50 | 125:1 to 1:25 |
| (5.1) spinosyns | 500:1 to 1:50 | 125:1 to 1:25 |
| (6.1) cyclodiene organochlorines | 500:1 to 1:50 | 125:1 to 1:25 |
| (6.2) fiproles | 500:1 to 1:200 | 125:1 to 1:50 |
| (7.1) mectins | 500:1 to 1:50 | 125:1 to 1:25 |
| (8) juvenile hormone mimetics | 500:1 to 1:50 | 125:1 to 1:25 |
| (9.1) diacylhydrazines | 500:1 to 1:50 | 125:1 to 1:25 |
| (10.1) benzoylureas | 500:1 to 1:50 | 125:1 to 1:25 |
| (10.2) buprofezin | 500:1 to 1:50 | 125:1 to 1:25 |

TABLE 2-continued

Mixing ratios

| Mixing partner (group) | Preferred mixing ratio | Particularly preferred mixing ratio |
|---|---|---|
| (10.3) cyromazine | 500:1 to 1:50 | 125:1 to 1:25 |
| (11.1) diafenthiuron | 500:1 to 1:50 | 125:1 to 1:25 |
| (11.2) organotins | 500:1 to 1:50 | 125:1 to 1:25 |
| (12.1) pyrroles | 500:1 to 1:50 | 125:1 to 1:25 |
| (12.2) dinitrophenols | 500:1 to 1:50 | 125:1 to 1:25 |
| (13.1) METIs | 500:1 to 1:50 | 125:1 to 1:25 |
| (13.2) hydramethylnone | 500:1 to 1:50 | 125:1 to 1:25 |
| (13.3) dicofol | 500:1 to 1:50 | 125:1 to 1:25 |
| (14) rotenone | 500:1 to 1:50 | 125:1 to 1:25 |
| (15.1) acequinocyl, fluacrypyrim | 500:1 to 1:50 | 125:1 to 1:25 |
| (16.1) Bacillus thuringiensis strains | 500:1 to 1:50 | 125:1 to 1:25 |
| (17.1) tetronic acids | 500:1 to 1:50 | 125:1 to 1:25 |
| (17.2) tetramic acids | 500:1 to 1:50 | 125:1 to 1:25 |
| (18) flonicamid | 500:1 to 1:50 | 125:1 to 1:25 |
| (19) amitraz | 500:1 to 1:50 | 125:1 to 1:25 |
| (20) propargite | 500:1 to 1:50 | 125:1 to 1:25 |
| (21) phthalamide | 500:1 to 1:50 | 125:1 to 1:25 |
| (22) nereistoxin analogues | 500:1 to 1:50 | 125:1 to 1:25 |
| (23) biologicals, hormones, pheromones | 500:1 to 1:50 | 125:1 to 1:25 |
| (24.1) fumigants | 500:1 to 1:50 | 125:1 to 1:25 |
| (24.2) selective antifeedants | 500:1 to 1:50 | 125:1 to 1:25 |
| (24.3) mite growth inhibitors | 500:1 to 1:50 | 125:1 to 1:25 |

The active compound combinations according to the invention are suitable for controlling animal pests, preferably arthropods and nematodes, in particular nematodes and insects found in agriculture, in animal health, in forests, in the protection of stored products and materials and in the hygiene sector. They are active against normally sensitive and resistant species, and against all or individual developmental stages. The abovementioned pests include:

From the order of the Isopoda, for example, *Oniscus asellus, Armadillidium vulgare, Porcellio scaber.*

From the order of the Diplopoda, for example, *Blaniulus guttulatus.*

From the order of the Chilopoda, for example, *Geophilus carpophagus, Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp., *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp., *Damalinia* spp.

From the order of the Thysanoptera, for example, *Hercinothrips femoralis, Thrips tabaci, Thrips palmi, Frankliniella accidentalis.*

From the order of the Heteroptera, for example, *Eurygaster* spp., *Dysdercus intermedius, Piesma quadrata, Cimex lectularius, Rhodnius prolixus, Triatoma* spp.

From the order of the *Homoptera*, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium comi, Saissetia oleae, Laodelphax striatellus, Nilaparvata lugens, Aonidiella aurantii, Aspidiotus hederae, Pseudococcus* spp., *Psylla* spp.

From the order of the *Lepidoptera*, for example, *Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofinannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus.*

From the order of the *Hymenoptera*, for example, *Diprion* spp., *Hoplocampa* spp., *Lasius* spp., *Monomorium pharaonis, Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.

From the order of the *Siphonaptera*, for example, *Xenopsylla cheopis, Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The phytoparasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

The active compound combinations can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are prepared in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics and chlorinated aliphatic hydrocarbons such as chlorobenzenes, chloroethylenes and methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

Suitable solid carriers are:

for example ammonium salts and ground natural minerals such as kaolins, clays, talc, chalk, quartz, attapulgite, montmorillonite or diatomaceous earth, and ground synthetic minerals such as finely divided silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example non-ionic and anionic emulsifiers such as polyoxyethylene fatty acid esters, polyoxyethylene fatty alcohol ethers, for example alkylaryl polyglycol ethers, alkyl sulphonates, alkyl sulphates, aryl sulphonates, or else protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colourants such as inorganic pigments, for example iron oxide, titanium oxide and Prussian blue, and organic colourants such alizarin colourants, azo colourants and metal phthalocyanine colourants, and trace nutrients such as salts of iron, manganese, boron, copper, cobalt, molybdenum and zinc.

The formulations generally comprise between 0.1 and 95% by weight of active compound, preferably between 0.5 and 90%.

The active compound combinations according to the invention can be present in their commercially available formulations and in the use forms, prepared from these formulations, as a mixture with other active compounds, such as insecticides, attractants, sterilants, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms.

Mixtures with other known active compounds such as herbicides or with fertilizers and growth regulators are also possible.

When used as insecticides, the active compound combinations according to the invention can furthermore be present in their commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

The active compound combinations can be used as such, in the form of concentrates or generally customary formulations such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellant, if desired desiccants and UV stabilizers, and if desired colourants and pigments and other processing auxiliaries.

The insecticidal compositions or concentrates used for protecting wood and timber products comprise the active compound according to the invention in a concentration of 0.0001 to 95% by weight, in particular 0.001 to 60% by weight.

The amount of composition or concentrate employed depends on the species and the abundance of the insects and on the medium. The optimal quantity to be employed can be determined in each case by test series upon application. In general, however, it will suffice to employ 0.0001 to 20% by weight, preferably 0.001 to 10% by weight, of the active compound, based on the material to be protected.

A suitable solvent and/or diluent is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents with an evaporation number of above 35 and a flash point of above 30° C., preferably above 45° C. Such oily and oil-type solvents which are insoluble in water and of low volatility and which are used are suitable mineral oils or their aromatic fractions or mineral-oil-containing solvent mixtures, preferably white spirit, petroleum and/or alkylbenzene.

Mineral oils with a boiling range of 170 to 220° C., white spirit with a boiling range of 170 to 220° C., spindle oil with a boiling range of 250 to 350° C., petroleum and aromatics with a boiling range of 160 to 280° C., oil of turpentine, and the like are advantageously used.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene are used.

The organic oily or oil-type solvents of low volatility and with an evaporation number of above 35 and a flash point of above 30° C., preferably above 45° C., can be replaced in part by organochemical solvents of high or medium volatility, with the proviso that the solvent mixture also has an evaporation number of above 35 and a flash point of above 30° C., preferably above 45° C., and that the mixture is soluble or emulsifiable in this solvent mixture.

In a preferred embodiment, some of the organochemical solvent or solvent mixture or an aliphatic polar organochemical solvent or solvent mixture is replaced. Aliphatic organochemical solvents which contain hydroxyl and/or ester and/or ether groups are preferably used, such as, for example, glycol ethers, esters or the like.

Organochemical binders used for the purposes of the present invention are the synthetic resins and/or binding drying oils which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin employed as binder can be employed in the form of an emulsion, dispersion or solution. Bitumen or bituminous substances may also be used as binders, in amounts of up to 10% by weight. In addition, colourants, pigments, water repellants, odour-masking agents, and inhibitors or anticorrosive agents and the like, all of which are known per se, can be employed.

In accordance with the invention, the composition or the concentrate preferably comprises, as organochemical binder, at least one alkyd resin or modified alkyd resin and/or a drying vegetable oil. Alkyd resins which are preferably used in accordance with the invention are those with an oil content of over 45% by weight, preferably 50 to 68% by weight.

Some or all of the abovementioned binder can be replaced by a fixative (mixture) or a plasticizer (mixture). These additives are intended to prevent volatilization of the active compounds, and also crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, phosphoric esters such as tributyl phosphate, adipic esters such as di(2-ethylhexyl) adipate, stearates such as butyl stearate or amyl stearate, oleates such as butyl oleate, glycerol ethers or higher-molecular-weight glycol ethers, glycerol esters and p-toluenesulphonic esters.

Fixatives are based chemically on polyvinyl alkyl ethers such as, for example, polyvinyl methyl ether, or ketones such as benzophenone and ethylenebenzophenone.

Other suitable solvents or diluents are, in particular, water, if appropriate as a mixture with one or more of the abovementioned organochemical solvents or diluents, emulsifiers and dispersants.

The active compound combinations are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests. They are active against sensitive and resistant species and against all developmental stages.

These pests include:

From the order of the Scorpionidea, for example, *Buthus occitanus*.

From the order of the Acarina, for example, *Argas persicus*, *Argas reflexus*, *Bryobia* ssp., *Dermanyssus gallinae*, *Glyciphagus domesticus*, *Ornithodorus moubat*, *Rhipicephalus sanguineus*, *Trombicula alfreddugesi*, *Neutrombicula autumnalis*, *Dermatophagoides pteronissimus*, *Dermatophagoides forinae*.

From the order of the Araneae, for example, *Aviculariidae*, *Araneidae*.

From the order of the Opiliones, for example, *Pseudoscorpiones chelifer*, *Pseudoscorpiones cheiridium*, *Opiliones phalangium*.

From the order of the Isopoda, for example, *Oniscus asellus*, *Porcellio scaber*.

From the order of the Diplopoda, for example, *Blaniulus guttulatus*, *Polydesmus* spp.

From the order of the Chilopoda, for example, *Geophilus* spp.

From the order of the Zygentoma, for example, *Ctenolepisma* spp., *Lepisma saccharina*, *Lepismodes inquilinus*.

From the order of the Blattaria, for example, *Blatta orientalies*, *Blattella germanica*, *Blattella asahinai*, *Leucophaea maderae*, *Panchlora* spp., *Parcoblatta* spp., *Periplaneta australasiae*, *Periplaneta americana*, *Periplaneta brunnea*, *Periplaneta fuliginosa*, *Supella longipalpa*.

From the order of the Saltatoria, for example, *Acheta domesticus*.

From the order of the Dennaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae*, *Necrobia* spp., *Ptinus* spp., *Rhizopertha dominica*, *Sitophilus granarius*, *Sitophilus oryzae*, *Sitophilus zeamais*, *Stegobium paniceum*.

From the order of the Diptera, for example, *Aedes aegypti*, *Aedes albopictus*, *Aedes taeniorhynchus*, *Anopheles* spp., *Calliphora erythrocephala*, *Chrysozona pluvialis*, *Culex quinquefasciatus*, *Culex pipiens*, *Culex tarsalis*, *Drosophila* spp., *Fannia canicularis*, *Musca domestica*, *Phlebotomus* spp., *Sarcophaga camaria*, *Simulium* spp., *Stomoxys calcitrans*, *Tipula paludosa*.

From the order of the Lepidoptera, for example, *Achroia grisella*, *Galleria mellonella*, *Plodia interpunctella*, *Tinea cloacella*, *Tinea pellionella*, *Tineola bisselliella*.

From the order of the Siphonaptera, for example, *Ctenocephalides canis*, *Ctenocephalides felis*, *Pulex irritans*, *Tunga penetrans*, *Xenopsylla cheopis*.

From the order of the Hymenoptera, for example, *Camponotus herculeanus*, *Lasius fuliginosus*, *Lasius niger*, *Lasius umbratus*, *Monomorium pharaonis*, *Paravespula* spp., *Tetramorium caespitum*.

From the order of the Anoplura, for example, *Pediculus humanus capitis*, *Pediculus humanus corporis*, *Phthirus pubis*.

From the order of the Heteroptera, for example, *Cimex hemipterus*, *Cimex lectularius*, *Rhodinus prolixus*, *Triatoma infestans*.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The mixtures according to the invention are particularly suitable for treating seed. Here, the combinations according to the invention mentioned above as preferred or particularly preferred may be mentioned as being preferred. Thus, a large part of the damage to crop plants which is caused by pests occurs as early as when the seed is attacked during storage and after the seed is introduced into the soil, and during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of pests by treating the seeds of plants has been known for a long time and is subject-matter of continuous improvements. However, the treatment of seed frequently entails a series of problems which cannot always be solved in a satisfactory manner. Thus, it is desirable to develop methods for protecting the seed and the germinating plant which dispense with the additional application of crop protection agents after sowing or after the emergence of the plants. It is furthermore desirable to optimize the amount of active compound employed in such a way as to provide maximum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and the germinating plant with a minimum of crop protection agents being employed.

Accordingly, the present invention relates in particular also to a method for protecting seed and germinating plants against attack by pests which comprises treating the seed with a composition according to the invention. The invention also relates to the use of the compositions according to the invention for treating seed for protecting the seed and the plant emerging therefrom against pests. Furthermore, the invention relates to seed treated with a composition according to the invention for protection against pests.

Furthermore, it must be considered as advantageous that the mixtures according to the invention can also be employed in particular in transgenic seed, the plants arising from this seed being capable of expressing a protein directed against pests. By treating such seed with the compositions according to the invention, certain pests can be controlled merely by the expression of the, for example, insecticidal protein, and additionally be protected by the compositions according to the invention against damage.

All plants and plant parts can be treated in accordance with the invention. Plants are to be understood as meaning in the present context all plants and plant populations such as desired and undesired wild plants or crop plants (inclusive of naturally occurring crop plants). Crop plants can be plants which can be obtained by conventional plant breeding and optimization methods or by biotechnological and genetic engineering methods or by combinations of these methods, inclusive of the transgenic plants and inclusive of the plant varieties protectable or not protectable by plant breeders' rights. Plant parts are to be understood as meaning all above-ground and below-ground parts and organs of plants, such as shoot, leaf, flower and root, examples which may be mentioned being leaves, needles, stalks, stems, flowers, fruit bodies, fruits and seeds, as well as roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on and, in the case of propagation material, in particular in the case of seed, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferred and to be treated according to the invention include all plants which, in the genetic modification, received genetic material which imparts particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), corn, soybeans, potatoes, cotton, oilseed rape and also fruit plants (with the fruits apples, pears, citrus fruits and grapes), and particular emphasis is given to corn, soybeans, potatoes, cotton and oilseed rape. Traits that are particularly emphasized are increased defence of the plants against insects by toxins formed in the plants, in particular those formed by the genetic material from *Bacillus thuringiensis* (for example by the genes CryIA(a), CryIA(b), CryIA(c), CryIIA, CryIIIA, CryIIB2, Cry9c Cry2Ab, Cry3Bb and CryIF and also combinations thereof) (hereinbelow referred to as "Bt plants"). Traits that are furthermore particularly emphasized are the increased tolerance of the plants to certain herbicidally active compounds, for example imidazolinones, sulfonylureas, glyphosate or phosphinotricin (for example the "PAT" gene).

The genes which impart the desired traits in question can also be present in combination with one another in the transgenic plants. Examples of "Bt plants" which may be mentioned are corn cultivars, cotton cultivars, soybean cultivars and potato cultivars which are sold under the trade names YIELD GARDQ (for example corn, cotton, soybeans), KnockOut® (for example corn), StarLink® (for example corn), Bollgard® (cotton), Nucotn® (cotton) and NewLeaf® (potato). Examples of herbicide-tolerant plants which may be mentioned are corn cultivars, cotton cultivars and soybean cultivars which are sold under the trade names Roundup Ready® (tolerance to glyphosate, for example corn, cotton, soybean), Liberty Link® (tolerance to phosphinotricin, for example oilseed rape), IMI® (tolerance to imidazolinones) and STS® (tolerance to sulfonylureas, for example corn). Herbicide-resistant plants (plants bred in a conventional manner for herbicide tolerance) which may be mentioned include the cultivars sold under the name Clearfield® (for example corn). Of course, these statements also apply to plant cultivars having these or still to be developed genetic traits, which plant cultivar/s will be developed and/or marketed in the future.

The plants listed can be treated according to the invention in a particularly advantageous manner with the active compound mixtures according to the invention. The preferred ranges stated above for the mixtures also apply to the treatment of these plants. Particular emphasis is given to the treatment of plants with the mixtures specifically mentioned in the present text.

The good insecticidal, acaricidal and nematicidal action of the active compound combinations according to the invention can be determined, for example, using the methods described in WO 2005/102056. Whereas the individual active compounds show weaknesses in their activity, the combinations show an activity which exceeds a simple addition of activities.

A synergistic effect in insecticides, acaricides and nematicides is always present when the insecticidal, acaricidal or nematicidal activity of the active compound combinations exceeds the total of the activities of the active compounds when applied individually.

The expected insecticidal, acaricidal or nematicidal activity for a given combination of two active compounds can be calculated according to S. R. Colby ("Calculating Synergistic and Antagonistic Responses of Herbicide Combinations", Weeds 1967, 15, 20-22) as follows:

If
X is the kill rate, expressed in % of the untreated control, when active compound A is applied at an application rate of m g/ha or at a concentration of m ppm,
Y is the kill rate, expressed in % of the untreated control, when active compound B is applied at an application rate of n g/ha or at a concentration of n ppm and
E is the kill rate, expressed in % of the untreated control, when active compounds A and B are applied at application rates of m and n g/ha or at a concentration of m and n ppm, then $$E = X + Y - \frac{X \cdot Y}{100}$$

If the actual insecticidal kill rate is greater than calculated, the kill of the combination is superadditive, i.e. there is a synergistic effect. In this case, the actual observed kill rate has to be greater than the value for the expected kill rate (E) calculated from the formula given above.

Example A

*Meloidogyne incognita* test (MELGIN)

To produce a suitable preparation of active compound, 1 part by weight of active compound is mixed with the stated amounts of solvent and emulsifier, and the concentrate is diluted with water to the desired concentration.

Lettuce seeds are dressed with the desired amount of formononetin. Vessels are filled with soil infected with mycorrhiza, active compound solution, *Meloidogyne incognita* egg/larvae suspension and the treated lettuce seeds. The lettuce seeds germinate and the plants develop. On the roots, galls are formed.

After the desired period of time, the nematicidal action is determined in % by the formation of galls. 100% means that no galls have been found; 0% means that the number of galls on the treated plants corresponds to that of the untreated control.

In this test, the following active compound combination in accordance with the present application showed a synergistically enhanced activity compared to the active compounds applied on their own:

TABLE A

Plant-damaging nematodes
*Meloidogyne incognita* test

| Active compound | Concentration | Effect in % after $21^d$ | |
|---|---|---|---|
| | | found* | calc.** |
| Formononetin of the formula (I) | 0.5 mg ai/seed | 3.3 | |
| Nemacur CS 240 | 0.03 ppm | 0 | |
| Formononetin + Nemacur CS 240 according to the invention | 0.5 mg ai/seed + 0.03 ppm | 43.3 | 3.3 |

*found = activity found
**calc. = activity calculated using Colby's formula

Example B

*Diabrotica* Test/Larvae in the Soil

Corn seeds were dressed with the formulated products in the desired concentration. Test vessels are filled with Mycorrhiza infected sandy loam and sown with 5 treated corn seeds per pot. The corn seeds germinate and the seedlings grow.

After 10 days 15 larvae of the Banded Cucumber Beetle (*Diabrotica balteata*) are placed in the soil.

After the desired period of time the level of activity expressed in % Abbott is determined. The mortality values determined thus are recalculated using the Colby-formular (see sheet 1).

According to the present application in this test e.g. the following combination shows a synergistic effect in comparison to the single compounds:

TABLE B

Plant damaging insects
*Diabrotica balteata* - test

| Compounds | concentration mg a.i***/seed | activity in % mortality after $10^d$ |
|---|---|---|
| Myconate (formononetin) FS 500 | 0.5 | 0 |

TABLE B-continued

| | Plant damaging insects *Diabrotica balteata* - test | | |
|---|---|---|---|
| Compounds | concentration mg a.i***/seed | activity in % mortality after 10$^d$ | |
| Imidacloprid FS 600 | 0.015 | 72.3 | |
| | | found* | calculated** |
| Myconate + Imidacloprid | 0.5 + 0.015 mg a.i***/ seed | 95.7 | 72.3 |

*found activity
**calculated activity according to the Colby formula
***a.i = active ingredient

The invention claimed is:

1. An active compound combination comprising formononetin of formula (1) and/or its salt thereof

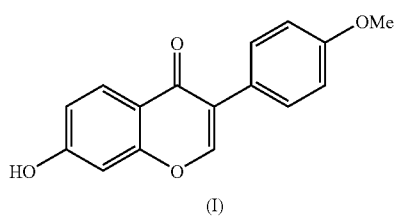

(I)

and at least one active insecticidal compound selected from groups (2) to (3) below:
group (2.1) chloronicotinyls and/or neonictonoids; and
group (3.2) organophosphates.

2. An active compound combination according to claim 1, wherein the active compound of groups (2) to (3) are selected from the list below:
(2.1.1) clothianidin;
(2.1.2) imidacloprid;
(2.1.3) thiacloprid;
(2.1.4) thiamethoxam;
(2.1.5) acetamiprid;
(2.1.6) dinotefuran;
(2.1.7) nitenpyram;
(2.1.8) imidaclothiz;
(3.2.1) tebupirimfos;
(3.2.2) cadusaphos;
(3.2.3) fosthiazate;
(3.2.4) ethopopphos; and
(3.2.5) fenamiphos.

3. An active compound combination according to claim 1, comprising formononetin and imidacloprid.

4. A synergistic active compound combination comprising an active compound combination according to claim 1.

5. A synergistic active compound combination according to claim 4, wherein the active compound of groups (2) to (3) are selected from the list below:
(2.1.1) clothianidin;
(2.1.2) imidacloprid;
(2.1.3) thiacloprid;
(2.1.4) thiamethoxam;
(2.1.5) acetamiprid;
(2.1.6) dinotefuran;
(2.1.7) nitenpyram;
(2.1.8) imidaclothiz;
(3.2.1) tebupirimfos;
(3.2.2) cadusaphos;
(3.2.3) fosthiazate;
(3.2.4) ethopopphos; and
(3.2.5) fenamiphos.

6. A synergistic active compound combination according to claim 4, comprising formononetin and imidacloprid.

7. A synergistic active compound combination according to claim 4, comprising formononetin and fenamiphos.

* * * * *